United States Patent
Tanaka et al.

(10) Patent No.: US 10,441,512 B2
(45) Date of Patent: *Oct. 15, 2019

(54) DENTAL CURABLE COMPOSITION AND METHOD OF MANUFACTURING SAME

(71) Applicant: GC Corporation, Tokyo (JP)

(72) Inventors: Hiroaki Tanaka, Tokyo (JP); Naofumi Matsumoto, Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/553,661

(22) PCT Filed: Mar. 15, 2016

(86) PCT No.: PCT/JP2016/058200
§ 371 (c)(1),
(2) Date: Aug. 25, 2017

(87) PCT Pub. No.: WO2016/152659
PCT Pub. Date: Sep. 29, 2016

(65) Prior Publication Data
US 2018/0049953 A1 Feb. 22, 2018

(30) Foreign Application Priority Data
Mar. 20, 2015 (JP) ................. 2015-058647

(51) Int. Cl.
*A61K 6/083* (2006.01)
*A61K 6/04* (2006.01)
*A61K 9/06* (2006.01)
*A61K 6/08* (2006.01)
*C08K 9/06* (2006.01)

(52) U.S. Cl.
CPC .......... *A61K 6/04* (2013.01); *A61K 6/08* (2013.01); *A61K 6/083* (2013.01); *C08K 9/06* (2013.01); *C08K 2201/005* (2013.01)

(58) Field of Classification Search
USPC ............ 523/115, 116, 117, 203; 433/228.1
See application file for complete search history.

(56) References Cited

U.S. PATENT DOCUMENTS

| 5,192,815 | A | 3/1993 | Okada et al. |
| 8,455,564 | B2 * | 6/2013 | Kuboe ............ A61K 6/0088 |
| | | | 106/35 |
| 9,855,196 | B2 * | 1/2018 | Kameya ............ A61K 6/083 |
| 2002/0072551 | A1 * | 6/2002 | Han ............ A61K 6/0017 |
| | | | 523/118 |
| 2010/0105802 | A1 | 4/2010 | Kuboe et al. |
| 2011/0046261 | A1 | 2/2011 | Kuboe et al. |
| 2015/0320646 | A1 | 11/2015 | Kameya et al. |

FOREIGN PATENT DOCUMENTS

| EP | 0530926 | 3/1993 |
| EP | 1897896 | 3/2008 |
| EP | 2926796 | 10/2015 |
| JP | H02-134307 | 5/1990 |
| JP | 2011-225526 | 11/2011 |
| WO | 2008/093596 | 8/2008 |
| WO | 2009/133912 | 11/2009 |
| WO | 2014/083842 | 6/2014 |

OTHER PUBLICATIONS

International Search Report for PCT/JP2016/058200 dated May 17, 2016.

* cited by examiner

*Primary Examiner* — Tae H Yoon
(74) *Attorney, Agent, or Firm* — IPUSA, PLLC

(57) ABSTRACT

A dental curable composition includes a polymerizable monomer, inorganic particles (A), and inorganic particles (B), wherein the inorganic particles (A) have a volume-median particle size of more than or equal to 0.1 μm and less than or equal to 0.9 μm and are surface-treated with a compound expressed by a general formula (1), the inorganic particles (B) have an average primary particle size of more than or equal to 5 nm and less than or equal to 50 nm, where at least one of a group expressed by a general formula (A) and a group expressed by a general formula (B) is present at surfaces of the inorganic particles (B), and the ratio of the mass of the inorganic particles (B) to the total mass of the inorganic particles (A) and the inorganic particles (B) is more than or equal to 0.02 and less than or equal to 0.05.

4 Claims, No Drawings

DENTAL CURABLE COMPOSITION AND METHOD OF MANUFACTURING SAME

CROSS-REFERENCE TO RELATED APPLICATIONS

This application is a national stage filing under 35 U.S.C. 371 of International Patent Application No. PCT/JP2016/058200, filed Mar. 15, 2016, which claims priority to Japanese Patent Application No. 2015-058647, filed Mar. 20, 2015. The entire disclosures of the foregoing applications are hereby incorporated herein by reference.

TECHNICAL FIELD

The present invention relates to dental curable compositions and methods of manufacturing a dental curable composition.

BACKGROUND ART

Flowable composite resins generally include a polymerizable monomer and an inorganic filler, and are widely used as materials for filling in and repairing lost portions of teeth or dental caries.

Patent Document 1 discloses, as a dental curable composition, a dental curable composition including a polymerizable monomer (A), irregularly-shaped inorganic particles (B) having an average particle size of 0.1 to 0.3 μm and surface-treated with a particular silane coupling agent (a), and inorganic ultrafine particles (C) having an average particle size of 5 to 50 nm and surface-treated with a particular silane coupling agent (b). The dental curable composition contains 92.5 to 98 wt % of the irregularly-shaped inorganic particles (B) and 2 to 7.5 wt % of the inorganic ultrafine particles (C) relative to the amount of total inorganic particles. The dental curable composition has a consistency of 25 to 55.

PRIOR ART DOCUMENT

Patent Document

[Patent Document 1] International Publication No. WO 2014/083842

SUMMARY OF THE INVENTION

Problems to be Solved by the Invention

There is, however, a problem in that polishability, abrasion resistance, formability and handleability, and flexural strength cannot be satisfied at the same time.

In view of the above-described problem of the conventional art, an embodiment of the present invention has an object of providing a flowable composite resin that can satisfy polishability, abrasion resistance, formability and handleability, and flexural strength at the same time.

MEANS FOR SOLVING THE PROBLEMS

According to an embodiment of the present invention, a dental curable composition includes a polymerizable monomer, inorganic particles (A), and inorganic particles (B), wherein the inorganic particles (A) have a volume-median particle size of more than or equal to 0.1 μm and less than or equal to 0.9 μm and are surface-treated with a compound expressed by a general formula

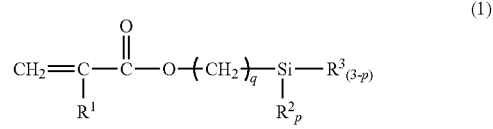

(1)

(where $R^1$ is a hydrogen atom or a methyl group, $R^2$ is a hydrolyzable group, $R^3$ is a hydrocarbon group having 1 to 6 carbon atoms, p is 2 or 3, and q is an integer greater than or equal to 8 and smaller than or equal to 13), the inorganic particles (B) have an average primary particle size of more than or equal to 5 nm and less than or equal to 50 nm, where at least one of a group expressed by a general formula

(A)

(where $R^4$ and $R^5$ are independently a methyl group or an ethyl group) and a group expressed by a general formula

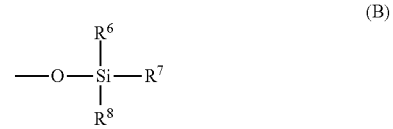

(B)

(where $R^6$, $R^7$, and $R^8$ are independently a methyl group or an ethyl group) is present at surfaces of the inorganic particles (B), and a ratio of a mass of the inorganic particles (B) to a total mass of the inorganic particles (A) and the inorganic particles (B) is more than or equal to 0.02 and less than or equal to 0.05.

According to an embodiment of the present invention, a method of manufacturing a dental curable composition includes a step of mixing a polymerizable monomer, inorganic particles (A), and inorganic particles (B), wherein the inorganic particles (A) have a volume-median particle size of more than or equal to 0.1 μm and less than or equal to 0.9 μm and are surface-treated with a compound expressed by a general formula

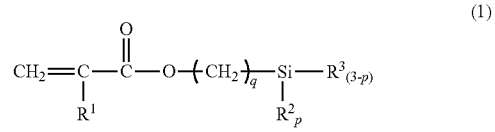

(1)

(where $R^1$ is a hydrogen atom or a methyl group, $R^2$ is a hydrolyzable group, $R^3$ is a hydrocarbon group having 1 to 6 carbon atoms, p is 2 or 3, and q is an integer greater than or equal to 8 and smaller than or equal to 13), the inorganic particles (B) have an average primary particle size of more than or equal to 5 nm and less than or equal to 50 nm, where at least one of a group expressed by a general formula

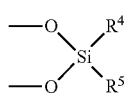

(where $R^4$ and $R^5$ are independently a methyl group or an ethyl group) and a group expressed by a general formula

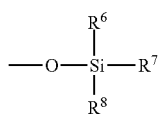

(where $R^6$, $R^7$, and $R^8$ are independently a methyl group or an ethyl group) is present at surfaces of the inorganic particles (B), and the ratio of the mass of the inorganic particles (B) to the total mass of the inorganic particles (A) and the inorganic particles (B) is more than or equal to 0.02 and less than or equal to 0.05.

EFFECTS OF THE INVENTION

According to an embodiment of the present invention, it is possible to provide a flowable composite resin that can satisfy polishability, abrasion resistance, formability and handleability, and flexural strength at the same time.

Embodiment of the Invention

Next, an embodiment of the present invention is described.

A dental curable composition includes a polymerizable monomer, inorganic particles (A), and inorganic particles (B).

The inorganic particles (A) are surface-treated with a compound expressed by a general formula (1). Therefore, it is possible to achieve both the flexural strength and the formability and handleability of a flowable composite resin.

The volume-median particle size of the inorganic particles (A) is 0.1 to 0.9 μm, and is preferably 0.15 to 0.70 μm. If the volume-median particle size of the inorganic particles (A) is less than 0.1 μm, the consistency of a flowable composite resin decreases. If the volume-median particle size of the inorganic particles (A) exceeds 0.9 μm, the abrasion resistance, the polishability, and the formability and handleability of a flowable composite resin are degraded.

The volume-median particle size of the inorganic particles (A) can be measured by laser diffraction scattering.

At least one of a group expressed by a general formula (A) and a group expressed by a general formula (B) is present at surfaces of the inorganic particles (B). Therefore, it is possible to increase the flexural strength of a flowable composite resin.

The average primary particle size of the inorganic particles (B) is 5 to 50 nm, and is preferably 5 to 20 nm. If the average primary particle size of the inorganic particles (B) is less than 5 nm, manufacturing becomes difficult. If the average primary particle size of the inorganic particles (B) exceeds 50 nm, the formability and handleability of a flowable composite resin are degraded.

The average primary particle size of the inorganic particles (B) is the average value of the primary particle diameters of 100 inorganic particles (B) randomly selected after taking electron micrographs.

The ratio of the mass of the inorganic particles (B) to the total mass of the inorganic particles (A) and the inorganic particles (B) is 0.02 to 0.05. If the ratio of the mass of the inorganic particles (B) to the total mass of the inorganic particles (A) and the inorganic particles (B) is less than 0.02 or exceeds 0.05, the formability and handleability of a flowable composite resin are degraded.

Next, the polymerizable monomer, the inorganic particles (A), and the inorganic particles (B) are described.

The refractive index of the polymerizable monomer after polymerization is normally 1.52 to 1.58, and is preferably 1.53 to 1.58.

The refractive index means a refractive index measured using an Abbe refractometer at 25° C.

The polymerizable monomer is preferably a radical polymerizable monomer.

Polymerizable monomers are not limited in particular, and include esters of α-cyanoacrylic acid, (meth)acrylic acid, α-haloacrylic acid, crotonic acid, cinnamic acid, sorbic acid, maleic acid, itaconic acid, etc., (meth)acrylamide, (meth)acrylamide derivatives, vinyl esters, vinyl ethers, mono-N-vinyl derivatives, and styrene derivatives, of which two or more may be used in combination. Among these, (meth) acrylic acid esters and (meth)acrylamide derivatives are preferable, and (meth)acrylic acid esters are more preferable.

Monofunctional (meth)acrylic acid esters and (meth)acrylamide derivatives include methyl (meth)acrylate, isobutyl (meth)acrylate, benzyl (meth)acrylate, lauryl (meth)acrylate, 2,3-dibromopropyl (meth)acrylate, 2-hydroxyethyl (meth) acrylate, 6-hydroxyhexyl (meth)acrylate, 10-hydroxydecyl (meth)acrylate, propylene glycol mono(meth)acrylate, glycerin mono(meth)acrylate, erythritol mono (meth)acrylate, N-methylol(meth)acrylamide, N-hydroxyethyl(meth)acrylamide, N-(dihydroxyethyl) (meth)acrylamide, (meth)acryloyloxydodecylpyridinium bromide, (meth)acryloyloxydodecylpyridinium chloride, (meth)acryloyloxyhexadecylpyridinium chloride, and (meth)acryloyloxydecylammonium chloride.

Difunctional (meth)acrylic acid esters include ethylene glycol di(meth)acrylate, triethylene glycol di(meth)acrylate, propylene glycol di(meth)acrylate, neopentyl glycol di(meth)acrylate, 1,6-hexanediol di(meth)acrylate, 1,10-decanediol di(meth)acrylate, 2,2-bis[4-[3-(meth)acryloyloxy-2-hydroxypropoxy]phenyl]propane, 2,2-bis[4-(2-(meth)acryloyloxyethoxy)phenyl]propane, 2,2-bis[4-(meth)acryloyloxypolyethoxyphenyl]propane, 1,2-bis[3-(meth)acryloyloxy-2-hydroxypropoxy]ethane, pentaerythritol di(meth)acrylate, and [2,2,4-trimethylhexamethylene bis(2-carbamoyloxyethyl)]di(meth)acrylate.

Tri- or higher-functional (meth)acrylic acid esters include trimethylolpropane tri(meth)acrylate, trimethylolethane tri (meth)acrylate, tetramethylolmethane tri(meth)acrylate, pentaerythritol tetra(meth)acrylate, dipentaerythritol hexa (meth)acrylate, N,N'-(2,2,4-trimethylhexamethylene)bis[2-(aminocarboxy)propane-1,3-diol]tetramethacrylate, and 1,7-diacryloyloxy-2,2,6,6-tetraacryloyloxymethyl-4-oxyheptane.

The ratio of the mass of the polymerizable monomer to the total mass of the inorganic particles (A) and the inorganic particles (B) is normally 0.25 to 0.5, and is preferably 0.3 to 0.45.

The inorganic particles (A) may be spherical, but are preferably irregularly shaped. This increases the specific surface area of the inorganic particles (A) to increase the bondability with the polymerizable monomer, thus making it possible to increase the flexural strength.

$R^2$ in the general formula (1) is not limited in particular, and includes alkoxy groups such as a methoxy group, an ethoxy group, and a butoxy group, a chlorine atom, and an isocyanate group.

$R^3$ in the general formula (1) is not limited in particular, and includes alkyl groups having 1 to 6 carbon atoms, alkenyl groups having 2 to 6 carbon atoms, and alkynyl groups having 2 to 6 carbon atoms.

Alkyl groups having 1 to 6 carbon atoms may be linear, branched, or cyclic, and include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, an n-hexyl group, a cyclopropyl group, a cyclobutyl group, a cyclopentyl group, and a cyclohexyl group.

Alkenyl groups having 2 to 6 carbon atoms may be linear, branched, or cyclic, and include a vinyl group, an allyl group, a methylvinyl group, a butenyl group, a pentenyl group, a hexenyl group, a cyclopropenyl group, a cyclobutenyl group, a cyclopentenyl group, and a cyclohexenyl group.

Alkynyl groups having 2 to 6 carbon atoms may be linear, branched, or cyclic, and include an ethynyl group, a 1-propynyl group, a 2-propynyl group, a 1-butynyl group, a 1-methyl-2-propynyl group, a 2-butynyl group, a 3-butynyl group, a 1-pentynyl group, a 1-ethyl-2-propynyl group, a 2-pentynyl group, a 3-pentynyl group, a 1-methyl-2-butynyl group, a 4-pentynyl group, a 1-methyl-3-butynyl group, a 2-methyl-3-butynyl group, a 1-hexynyl group, a 2-hexynyl group, a 1-ethyl-2-butynyl group, a 3-hexynyl group, a 1-methyl-2-pentynyl group, a 1-methyl-3-pentynyl group, a 4-methyl-1-pentynyl group, a 3-methyl-1-pentynyl group, a 5-hexynyl group, and a 1-ethyl-3-butynyl group.

Compounds expressed by the general formula (1) are not limited in particular, and include 8-methacryloyloxyoctyltrimethoxysilane, 9-methacryloyloxynonyltrimethoxysilane, 10-methacryloyloxydecyltrimethoxysilane, 11-methacryloyloxyundecyltrimethoxysilane, 11-methacryloyloxyundecyldichloromethylsilane, 11-methacryloyloxyundecyltrichlorosilane, 11-methacryloyloxyundecyldimethoxymethylsilane, 12-methacryloyloxydodecyltrimethoxysilane, and 13-methacryloyloxytridecyltrimethoxysilane, of which two or more may be used in combination. Among these, 8-methacryloyloxyoctyltrimethoxysilane, 9-methacryloyloxynonyltrimethoxysilane, 10-methacryloyloxydecyltrimethoxysilane, and 11-methacryloyloxyundecyltrimethoxysilane are preferable.

Methods of surface-treating the inorganic particles (A) are not limited in particular, and include a method by which the inorganic particles (A) before being surface-treated are sprayed with a solution of the compound expressed by the general formula (1) diluted with a solvent while being stirred in a mixing tank and are heated and dried for a certain time in the tank while being kept stirred and a method by which the inorganic particles (A) before being surface-treated and the compound expressed by the general formula (1) are stirred and mixed in a solvent and are thereafter heated to be dried.

The mass ratio of the compound expressed by the general formula (1) to the inorganic particles (A) before being surface-treated is normally 0.005 to 0.15, and is preferably 0.01 to 0.13.

The refractive index of the inorganic particles (A) is normally 1.52 to 1.58, and is preferably 1.53 to 1.58.

The difference between the refractive index of the polymerizable monomer after polymerization and the refractive index of the inorganic particles (A) is normally 0.03 or less.

Materials for the inorganic particles (A) are not limited in particular, and include various kinds of glass that contain silica as a principal component and contain, on an as-needed basis, an oxide of a heavy metal, boron, aluminum or the like (such as E glass, barium glass, and lanthanum glass-ceramics), various kinds of ceramics, composite oxides (such as silica-titania composite oxide and silica-zirconia composite oxide), kaolin, clay minerals (such as montmorillonite), mica, ytterbium fluoride, and yttrium fluoride, of which two or more may be used in combination.

Commercially available products of the inorganic particles (A) include G018-053, GM27884, 8235 and GM31684 (all of which are manufactured by Schott AG) and E 2000 and E 3000 (both of which are manufactured by ESSTECH, Inc.).

The inorganic particles (B) may be either spherical or irregularly shaped. Furthermore, the inorganic particles (B) may be either primary particles that are not aggregated or secondary particles into which primary particles aggregate.

When the inorganic particles (B) are irregularly shaped, the primary particle size is the average value of the long diameter and the short diameter of the inorganic particles (B).

Methods of surface-treating the inorganic particles (B) are not limited in particular, and include a method by which the inorganic particles (B) before being surface-treated are sprayed with a solution of a silane coupling agent diluted with a solvent while being stirred in a mixing tank and are heated and dried for a certain time in the tank while being kept stirred and a method by which the inorganic particles (B) before being surface-treated and a silane coupling agent are stirred and mixed in a solvent and are thereafter heated to be dried.

Silane coupling agents are not limited in particular as long as they can introduce at least one of the group expressed by the chemical formula (A) and the group expressed by the chemical formula (B) onto a surface, and include dimethyldichlorosilane and hexamethyldisilazane.

Materials for the inorganic particles (B) are not limited in particular, and include inorganic oxides such as silica, alumina, titania, and zirconia and composite oxides thereof, calcium phosphate, hydroxylapatite, yttrium fluoride, ytterbium fluoride, barium titanate, and potassium titanate. Among these, silica, alumina, titania, silica-alumina composite oxide, and silica-zirconia composite oxide are preferable.

Commercially available products of the inorganic particles (B) include Aerosil R812, R972, and RX-50 (all of which are manufactured by Nippon Aerosil Co., Ltd.).

The refractive index of the inorganic particles (B) is normally 1.43 to 1.50, and is preferably 1.43 to 1.46.

The difference between the refractive index of the polymerizable polymer after polymerization and the refractive index of the inorganic particles (B) is normally 0.05 or more.

The dental curable composition may further include a polymerization initiator.

In the case of curing the dental curable composition at room temperature, a redox polymerization initiator can be used.

Redox polymerization initiators are not limited in particular, and include organic peroxide/amine systems and organic peroxide/amine/sulfinic acid (or a salt thereof) systems.

In the case of using a redox polymerization initiator, an oxidant and a reductant need to be in package form of being separately packaged and be mixed up immediately before use.

Oxidants are not limited in particular, and include organic peroxides such as diacyl peroxides, peroxyesters, peroxycarbonates, dialkyl peroxides, peroxyketals, ketone peroxides, and hydroperoxides.

Diacyl peroxides include benzoyl peroxide, 2,4-dichlorobenzoyl peroxide, m-toluoyl peroxide, and lauroyl peroxide.

Peroxyesters include t-butyl peroxybenzoate, di-t-butyl peroxyisophthalate, and t-butyl peroxy-2-ethylhexanoate.

Peroxycarbonates include t-butyl peroxy isopropyl carbonate.

Dialkyl peroxides include dicumyl peroxide, di-t-butyl peroxide, and 2,5-dimethyl-2,5-bis(benzoylperoxy)hexane.

Peroxyketals include 1,1-bis(t-butylperoxy)-3,3,5-trimethylcyclohexane.

Ketone peroxides include methyl ethyl ketone peroxide.

Hydroperoxides include t-butyl hydroperoxide.

Reductants are not limited in particular, and include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-p-toluidine, N,N-bis(2-hydroxyethyl)-3,5-dimethylaniline, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-diisopropylaniline, N,N-bis(2-hydroxyethyl)-3,5-di-t-butylaniline, ethyl 4-dimethylaminobenzoate, n-butoxyethyl 4-dimethylaminobenzoate, 2-methacryloyloxyethyl 4-dimethylaminobenzoate, trimethylamine, triethylamine, N-methyldiethanolamine, N-ethyldiethanolamine, N-n-butyldiethanolamine, N-lauryldiethanolamine, triethanolamine, (2-dimethylamino)ethyl methacrylate, N-methyldiethanolamine dimethacrylate, N-ethyldiethanolamine dimethacrylate, triethanolamine monomethacrylate, triethanolamine dimethacrylate, and triethanolamine trimethacrylate.

As redox polymerization initiators other than those described above, in addition to oxidation-reduction initiators such as cumenehydroperxide/thiourea systems, ascorbic acid/$Cu^{2+}$ salt systems, and organic sulfinic acid (or salt thereof)/amine/inorganic peroxide systems, tributylborane, organic sulfinic acid, etc., as well may be used.

In the case of curing the dental curable composition through exposure to visible light, a photopolymerization initiator can be used.

Photopolymerization initiators are not limited in particular, and include oxidation-reduction initiators such as α-diketone/reductant, ketal/reductant, and thioxanthone/reductant.

Alpha-diketones include camphorquinone, benzyl, and 2,3-pentanedione.

Ketals include benzyl dimethyl ketal and benzyl diethyl ketal.

Thioxanthone include 2-chlorothioxanthone and 2,4-diethylthioxantone.

Reductants include tertiary amines such as Michler's ketone, 2-(dimethylamino)ethyl methacrylate, N,N-bis [(meth)acryloyloxyethyl]-N-methylamine, ethyl N,N-dimethylaminobenzoate, butyl 4-dimethylaminobenzoate, butoxyethyl 4-dimethylaminobenzoate, N-methyldiethanolamine, 4-dimethylaminobenzophenone, N,N-bis(2-hydroxyethyl)-p-toluidine, and dimethylaminophenanthrol; aldehydes such as citronellal, lauryl aldehyde, phthaldialdehyde, dimethylaminobenzaldehyde, and terephthalaldehyde; and compounds having a thiol group, such as 2-mercaptobenzoxazole, decanethiol, 3-mercaptopropyltrimethoxysilane, 4-mercaptoacetophenone, thiosalicylic acid, and thiobenzoic acid.

An organic peroxide may be added to oxidation-reduction initiators.

In the case of curing the dental curable composition through exposure to ultraviolet radiation, a photopolymerization initiator can be used.

Photopolymerization initiators are not limited in particular, and include benzoin alkyl ethers, benzyl dimethyl ketals, acylphosphine oxides, and bisacylphosphine oxides.

Acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyl bis(2,6-dimethylphenyl)phosphonate, and 2,4,6-trimethylbenzoylethoxyphenylphosphine oxide.

Bisacylphosphine oxides include bis(2,6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl) phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, and bis(2,4,6-trimethylbenzoyl)phenylphosphine oxide.

(Bis)acylphosphine oxides may be substituted by a water-soluble substituent.

Furthermore, (bis)acylphosphine oxides may be used in combination with reductants such as amines, aldehydes, mercaptans, and sulfinic acid salts.

The mass ratio of the polymerization initiator to the polymerizable monomer is normally 0.001 to 0.1, and is preferably 0.002 to 0.05.

The dental curable composition may further include a polymerization inhibitor, an ultraviolet absorber, a fluorescent agent, and a pigment.

Polymerization inhibitors are not limited in particular, and include 3,5-dibutyl-4-hydroxytoluene, hydroquinone, dibutylhydroquinone, dibutylhydroquinone monomethyl ether, 2,6-t-butylphenol, and 4-methoxyphenol, of which two or more may be used in combination.

The dental curable composition may be either paste in which the inorganic particles (A) and the inorganic particles (B) are dispersed in the polymerizable monomer or a molded body in which the polymerizable monomer, the inorganic particles (A), and the inorganic particles (B) are dispersed in the cured polymerizable monomer.

For example, a cavity in the oral cavity can be treated by being directly filled with paste in which the inorganic particles (A) and the inorganic particles (B) are dispersed in the polymerizable monomer. Furthermore, after curing and molding paste in which the inorganic particles (A) and the inorganic particles (B) are dispersed in the polymerizable monomer outside the oral cavity, the molded body may be attached inside the oral cavity using a dental adhesive.

Here, when the dental curable composition is chemically polymerizable or when the dental curable composition is chemically polymerizable and photopolymerizable, a composition containing an oxidant and a composition containing a reductant need to be in package form of being separately packaged and be mixed up immediately before use of the dental curable composition.

The dental curable composition is preferably a flowable composite resin. At this point, the flowable composite resin may be either a one-agent type or a two-agent type.

The extrusion strength of the flowable composite resin is normally 10 kgf or less. This makes it possible to improve the formability and handleability of the flowable composite resin.

The flowable composite resin is provided, for example, in the form of a package that includes a syringe filled with the flowable composite resin, a plunger fitted into the syringe from the rear end side of the syringe, and a needle chip to be attached to the tip of the syringe.

The inner diameter of the needle of the needle chip is normally 0.3 to 0.9 mm.

When the flowable composite resin is a two-agent type, the package may include, for example, two syringes connected in parallel and two plungers connected in parallel, and a static mixer may be provided at the tips of the syringes.

EXAMPLES

The present invention is described in detail below with reference to examples and comparative examples, but is not limited to the examples. Part means part by mass.

[Manufacture of Inorganic Particles (A-1)]

Irregularly-shaped barium glass particles GM27884 NanoFine 180 (manufactured by Schott AG) having a volume-median particle size of 0.18 μm were surface-treated with 8-methacryloyloxyoctyltrimethoxysilane to obtain inorganic particles (A-1) having a volume-median particle size of 0.18 μm.

[Manufacture of Inorganic Particles (A-2)]

Inorganic particles (A-2) having a volume-median particle size of 0.4 μm were obtained in the same manner as the inorganic particles (A-1) except for using barium glass particles G018-053 Ultra Fine 0.4 (manufactured by Schott AG) having a volume-median particle size of 0.40 μm instead of irregularly-shaped barium glass particles GM27884 NanoFine 180 (manufactured by Schott AG) having a volume-median particle size of 0.18 μm.

[Manufacture of Inorganic Particles (A-3)]

Inorganic particles (A-3) having a volume-median particle size of 0.7 μm were obtained in the same manner as the inorganic particles (A-1) except for using barium glass particles G018-053 Ultra Fine 0.7 (manufactured by Schott AG) having a volume-median particle size of 0.70 μm instead of irregularly-shaped barium glass particles GM27884 NanoFine 180 (manufactured by Schott AG) having a volume-median particle size of 0.18 μm.

[Manufacture of Inorganic Particles (A-4)]

Inorganic particles (A-4) having a volume-median particle size of 0.18 μm were obtained in the same manner as the inorganic particles (A-1) except for using 3-methacryloyloxypropyltrimethoxysilane instead of 8-methacryloyloxyoctyltrimethoxysilane.

[Manufacture of Inorganic Particles (A-5)]

Inorganic particles (A-5) having a volume-median particle size of 0.4 μm were obtained in the same manner as the inorganic particles (A-2) except for using 3-methacryloyloxypropyltrimethoxysilane instead of 8-methacryloyloxyoctyltrimethoxysilane.

[Manufacture of Inorganic Particles (A-6)]

Inorganic particles (A-6) having a volume-median particle size of 0.7 μm were obtained in the same manner as the inorganic particles (A-3) except for using 3-methacryloyloxypropyltrimethoxysilane instead of 8-methacryloyloxyoctyltrimethoxysilane.

[Manufacture of Inorganic Particles (A-7)]

Inorganic particles (A-7) having a volume-median particle size of 2.0 μm were obtained in the same manner as the inorganic particles (A-1) except for using irregularly-shaped barium glass particles 8235 Ultra Fine 2.0 (manufactured by Schott AG) having a volume-median particle size of 2.0 μm instead of irregularly-shaped barium glass particles GM27884 NanoFine 180 (manufactured by Schott AG) having a volume-median particle size of 0.18 μm.

Table 1 shows characteristics of the inorganic particles (A).

TABLE 1

| Inorganic Particles | Volume-Median Particle Size [μm] | Surface Treatment Agent |
| --- | --- | --- |
| A-1 | 0.18 | 8-methacryloyloxyoctyltrimethoxysilane |
| A-2 | 0.40 | 8-methacryloyloxyoctyltrimethoxysilane |
| A-3 | 0.70 | 8-methacryloyloxyoctyltrimethoxysilane |
| A-4 | 0.18 | 3-methacryloyloxypropyltrimethoxysilane |
| A-5 | 0.40 | 3-methacryloyloxypropyltrimethoxysilane |
| A-6 | 0.70 | 3-methacryloyloxypropyltrimethoxysilane |
| A-7 | 2.0 | 8-methacryloyloxyoctyltrimethoxysilane |

[Volume-Median Particle Size of Inorganic Particles (A)]

15 mg of the inorganic particles (A) were added to 20 mL of a 0.2 mass % sodium hexametaphosphate solution, and the inorganic particles (A) were dispersed for 30 minutes using an ultrasonic disperser to obtain a dispersion of the inorganic particles (A). Then, the volume-median particle size of the inorganic particles (A) was measured using a laser diffraction particle size distribution analyzer LA-950 (manufactured by HORIBA, Ltd).

[Inorganic Particles (B-1)]

Silica particles Aerosil R812 (manufactured by Nippon Aerosil Co., Ltd.), having an average primary particle size of 7 nm and surface-treated with hexamethyldisilazane, were used as inorganic particles (B-1).

[Inorganic Particles (B-2)]

Silica particles Aerosil R972 (manufactured by Nippon Aerosil Co., Ltd.), having an average primary particle size of 16 nm and surface-treated with dimethyldichlorosilane, were used as inorganic particles (B-2).

[Inorganic Particles (B-3)]

Silica particles Aerosil OX-50 (manufactured by Nippon Aerosil Co., Ltd.) having an average primary particle size of 40 nm were treated with 3-methacryloyloxypropyltrimethoxysilane to obtain inorganic particles (B-3) having an average primary particle size of 40 nm.

Table 2 shows characteristics of the inorganic particles (B).

TABLE 2

| Inorganic Particles | Average Primary Particle Size [nm] | Surface Treatment Agent |
| --- | --- | --- |
| B-1 | 7 | Hexamethyldisilazane |
| B-2 | 16 | Dimethyldichlorosilane |
| B-3 | 40 | 3-methacryloyloxypropyltrimethoxysilane |

[Average Primary Particle Size of Inorganic Particles (B)]

Electron micrographs of 100 inorganic particles (B) were subjected to image analysis using image analysis software WinROOF (manufactured by MITANI Corporation), and thereafter, the average primary particle size of the inorganic particles (B) was calculated as a volume average particle size.

Example 1

30.4 parts of 2,2-bis[4-(2-methacryloyloxyethoxy)phenyl]propane (Bis-MEPP), 8.7 parts of [2,2,4-trimethylhexamethylene bis(2-carbamoyloxyethyl)]dimethacrylate (UDMA), and 4.3 parts of triethylene glycol di(meth)acrylate (TEGDMA) were mixed to obtain a polymerizable monomer.

An appropriate amount of each of camphorquinone, ethyl N,N-dimethylaminobenzoate, trimethyldiphenylphosphine oxide, and dibutylhydroxytoluene (BHT) was added to the polymerizable monomer to obtain a polymerizable monomer composition.

98.0 parts of the inorganic particles (A-1) and 2.0 parts of the inorganic particles (B-1) were added to the polymerizable monomer composition, and after mixing and kneading for homogeneity, vacuum defoaming was performed to obtain a flowable composite resin in paste form.

Example 2

A flowable composite resin in paste form was obtained in the same manner as in Example 1 except for changing the amounts of addition of the inorganic particles (A-1) and the inorganic particles (B-1) to 97.5 parts and 2.5 parts, respectively.

Example 3

A flowable composite resin in paste form was obtained in the same manner as in Example 1 except for changing the amounts of addition of Bis-MEPP, UDMA, and TEGDMA to 27.4 parts, 7.8 parts, and 3.9 parts, respectively, and using the inorganic particles (A-2) instead of the inorganic particles (A-1).

Example 4

A flowable composite resin in paste form was obtained in the same manner as in Example 3 except for changing the amounts of addition of the inorganic particles (A-2) and the inorganic particles (B-1) to 97.5 parts and 2.5 parts, respectively.

Example 5

A flowable composite resin in paste form was obtained in the same manner as in Example 3 except for using the inorganic particles (A-3) instead of the inorganic particles (A-2).

Example 6

A flowable composite resin in paste form was obtained in the same manner as in Example 5 except for changing the amounts of addition of the inorganic particles (A-3) and the inorganic particles (B-1) to 97.5 parts and 2.5 parts, respectively.

Example 7

A flowable composite resin in paste form was obtained in the same manner as in Example 3 except for changing the amounts of addition of the inorganic particles (A-2) and the inorganic particles (B-1) to 97.0 parts and 3.0 parts, respectively.

Example 8

A flowable composite resin in paste form was obtained in the same manner as in Example 3 except for changing the amounts of addition of the inorganic particles (A-2) and the inorganic particles (B-1) to 96.0 parts and 4.0 parts, respectively.

Example 9

A flowable composite resin in paste form was obtained in the same manner as in Example 3 except for changing the amounts of addition of the inorganic particles (A-2) and the inorganic particles (B-1) to 95.0 parts and 5.0 parts, respectively.

Example 10

A flowable composite resin in paste form was obtained in the same manner as in Example 1 except for changing the amounts of addition of the inorganic particles (A-1) and the inorganic particles (B-1) to 95.0 parts and 5.0 parts, respectively.

Example 11

A flowable composite resin in paste form was obtained in the same manner as in Example 5 except for changing the amounts of addition of the inorganic particles (A-3) and the inorganic particles (B-1) to 95.0 parts and 5.0 parts, respectively.

Example 12

A flowable composite resin in paste form was obtained in the same manner as in Example 3 except for using the inorganic particles (B-2) instead of the inorganic particles (B-1).

Example 13

A flowable composite resin in paste form was obtained in the same manner as in Example 9 except for using the inorganic particles (B-2) instead of the inorganic particles (B-1).

Comparative Example 1

A flowable composite resin in paste form was obtained in the same manner as in Example 2 except for using the inorganic particles (A-4) instead of the inorganic particles (A-1).

Comparative Example 2

A flowable composite resin in paste form was obtained in the same manner as in Example 4 except for using the inorganic particles (A-5) instead of the inorganic particles (A-2).

Comparative Example 3

A flowable composite resin in paste form was obtained in the same manner as in Example 6 except for using the inorganic particles (A-6) instead of the inorganic particles (A-3).

Comparative Example 4

A flowable composite resin in paste form was obtained in the same manner as in Example 3 except for changing the amounts of addition of the inorganic particles (A-2) and the inorganic particles (B-1) to 94.0 parts and 6.0 parts, respectively.

Comparative Example 5

A flowable composite resin in paste form was obtained in the same manner as in Example 3 except for using the inorganic particles (A-7) instead of the inorganic particles (A-2).

Comparative Example 6

A flowable composite resin in paste form was obtained in the same manner as in Comparative Example 2 except for changing the amounts of addition of Bis-MEPP, UDMA, and TEGDMA to 34.8 parts, 9.9 parts, and 4.9 parts, respectively.

Comparative Example 7

A flowable composite resin in paste form was obtained in the same manner as in Example 3 except for using the inorganic particles (B-3) instead of the inorganic particles (B-1).

Comparative Example 8

A flowable composite resin in paste form was obtained in the same manner as in Comparative Example 7 except for changing the amounts of addition of the inorganic particles (A-2) and the inorganic particles (B-3) to 96.0 parts and 4.0 parts, respectively.

Table 3 shows characteristics of the flowable composite resins of the examples and the comparative examples.

TABLE 3

| | Inorganic Particles | | | | |
|---|---|---|---|---|---|
| | A | B | Amount of Addition of A [part] | Amount of Addition of B [part] | Extrusion Strength [kgf] |
| Example 1 | A-1 | B-1 | 98.0 | 2.0 | 4 |
| Example 2 | A-1 | B-1 | 97.5 | 2.5 | 5 |
| Example 3 | A-2 | B-1 | 98.0 | 2.0 | 3 |
| Example 4 | A-2 | B-1 | 97.5 | 2.5 | 3 |
| Example 5 | A-3 | B-1 | 98.0 | 2.0 | 3 |
| Example 6 | A-3 | B-1 | 97.5 | 2.5 | 3 |
| Example 7 | A-2 | B-1 | 97.0 | 3.0 | 5 |
| Example 8 | A-2 | B-1 | 96.0 | 4.0 | 6 |
| Example 9 | A-2 | B-1 | 95.0 | 5.0 | 8 |
| Example 10 | A-1 | B-1 | 95.0 | 5.0 | 8 |
| Example 11 | A-3 | B-1 | 95.0 | 5.0 | 9 |
| Example 12 | A-2 | B-2 | 98.0 | 2.0 | 8 |
| Example 13 | A-2 | B-2 | 95.0 | 5.0 | 8 |
| Comparative Example 1 | A-4 | B-1 | 97.5 | 2.5 | 28 |
| Comparative Example 2 | A-5 | B-1 | 97.5 | 2.5 | 24 |
| Comparative Example 3 | A-6 | B-1 | 97.5 | 2.5 | 12 |
| Comparative Example 4 | A-2 | B-1 | 94.0 | 6.0 | 15 |
| Comparative Example 5 | A-7 | B-1 | 98.0 | 2.0 | 5 |
| Comparative Example 6 | A-5 | B-1 | 97.5 | 2.5 | 7 |
| Comparative Example 7 | A-2 | B-3 | 98.0 | 2.0 | 8 |
| Comparative Example 8 | A-2 | B-3 | 96.0 | 4.0 | 8 |

[Extrusion Strength]

Extrusion strength was evaluated using a cylindrical polyolefin resin syringe (an MI filling container of 7.7 mm in inner diameter and 78.6 mm in length), a cylindrical plunger fitted into the syringe from the rear end side of the syringe, and a needle chip (20G) to be attached to the tip of the syringe. Here, the needle of the needle chip is 0.65 mm in inner diameter and 13 mm in length, and is bent 50° at a position 7.5 mm from the tip. Furthermore, the syringe and the plunger are formed of a member opaque to environmental light.

First, after filling the syringe with 2.0 mL of a flowable composite resin, the needle chip was attached to the tip of the syringe, and the plunger was pushed to extrude the flowable composite resin from the tip of the needle chip. At this point, extrusion strength was measured at 25° C., using a universal testing machine AG-IS (manufactured by Shimadzu Corporation). Specifically, while vertically retaining the storage container, a crosshead to which a jig for compressive strength test was attached was lowered at 10 ram/min. to apply a load on and extrude the flowable composite resin, and a maximum load at the time was determined as extrusion strength. Extrusion strength of 10 kgf or less is determined as being acceptable.

Then, the flexural strength, the abrasion resistance, the polishability, the consistency, and the formability and handleability of the flowable composite resins were evaluated.

[Flexural Strength]

After filling a stainless steel mold of 2 mm×2 mm×25 mm with a flowable composite resin, the flowable composite resin was brought into press contact with slide glasses on the upper side and the lower side. Next, the flowable composite resin was cured by irradiating the upper surface and the lower surface at nine points on each surface with visible light for 10 seconds per point, using a G-Light Prima-II (manufactured by GC Corporation). Then, after being extracted from the mold, the cured product was stored in distilled water at 37° C. for 24 hours to obtain a test piece. At this point, five test pieces were made. Next, the flexural strength of the five test pieces was measured using a universal testing machine AG-IS (manufactured by Shimadzu Corporation) with the support span being 20 mm and the crosshead speed being 1 mm/min, and thereafter, the average value was calculated to be determined as flexural strength. A flexural strength of 160 MPa or more is determined as being acceptable.

[Abrasion Resistance]

After filling a dedicated mold with a flowable composite resin, the flowable composite resin was brought into press contact with slide glasses on the upper side and the lower side. Next, the upper surface and the lower surface of the flowable composite resin were irradiated with visible light for 10 seconds using a G-Light Prima-II (manufactured by GC Corporation) to cure the flowable composite resin. Furthermore, after being extracted from the mold, the cured product was stored in distilled water at 37° C. for 24 hours to obtain a test piece. Each test piece was attached to a bite abrasion tester (manufactured by TOKYO GIKEN, INC.), and after polishing an unpolymerized layer with #1000 abrasive paper, the overall length of the test piece before testing was measured. A slurry obtained by mixing and kneading the equal amounts of glycerin and Acricone AC (manufactured by Mitsubishi Rayon Co., Ltd.) was laid on the bite abrasion tester, and a test assuming 100,000 vertical and lateral bites was conducted against a PMMA plate. After the test, the overall length of each test piece was measured, and the abrasion resistance was evaluated by determining the difference between before and after the test as the amount of wear. A wear of 10 μm or less is determined as being acceptable.

[Polishability]

After filling a mold of 15 mm in diameter and 1.5 mm in thickness with a flowable composite resin, the flowable composite resin was brought into press contact with slide glasses on the upper side and the lower side. Next, the flowable composite resin was cured by irradiating the upper surface and the lower surface at nine points on each surface with visible light for 10 seconds per point, using a G-Light Prima-II (manufactured by GC Corporation). Furthermore, the cured product was extracted from the mold to obtain a test piece. Next, a smooth surface of the test piece was polished under a dry condition, using #600 abrasive paper. Furthermore, using MICROMOTOR LM-III (manufactured by GC Corporation), with water being injected, polishing was performed for 10 seconds at a rotational speed of approximately 10,000 rpm using PRE SHINE (manufactured by GC Corporation), and thereafter, polishing was performed for 10 seconds at a rotational speed of approximately 10,000 rpm using DIA SHINE (manufactured by GC Corporation). Furthermore, the glossiness of the polished surface was measured at a measurement angle of 60°, using a glossmeter VG-2000 (manufactured by NIPPON DENSHOKU INDUSTRIES CO., LTD.), and its ratio to that of a mirror serving as 100 was determined as glossiness. A glossiness of 60% or more is determined as being acceptable.

[Consistency]

After filling the syringe with a flowable composite resin, the flowable composite resin was left stationary for 2 hours at 25° C. Next, in a constant temperature and humidity dark room at 25° C. and 50% RH, 0.5 mL of the flowable composite resin were left stationary in a mound shape at the center of an OHP sheet of 5 cm×5 cm, and an OHP sheet of 5 cm×5 cm and a weight of 120 g were placed thereon. Furthermore, after the long diameter and the short diameter of the flowable composite resin after passage of 60 seconds were measured through a glass plate, the average value of the long diameter and the short diameter was calculated to be determined as consistency. Here, the long diameter means the longest one of the diameters passing through the center, and the short diameter means one perpendicular to the long diameter among the diameters passing through the center. A consistency of 25 to 35 mm is determined as being acceptable.

[Formability and Handleability]

Using the above-described syringe, plunger, and needle chip, 0.03 g of a flowable composite resin were extruded onto white mixing paper. At this point, the formability and handleability were evaluated. The formability and handleability were determined based on the following criteria.

1: The viscosity of a flowable composite resin is appropriate to make it possible to easily build up and correct the shape of the flowable composite resin.

2: The viscosity of a flowable composite resin is somewhat high to make it difficult to correct the shape of the flowable composite resin, or the viscosity of a flowable composite resin is somewhat low to make it difficult to build up the flowable composite resin.

3: The viscosity of a flowable composite resin is high to make it impossible to correct the shape of the flowable composite resin, or the viscosity of a flowable composite resin is low to make it impossible to build up the flowable composite resin.

Table 4 shows the evaluation results of the flexural strength, the abrasion resistance, the polishability, the consistency, and the formability and handleability of the flowable composite resins.

TABLE 4

| | Flexural Strength [MPa] | Abrasion Resistance [μm] | Polishability [%] | Consistency [mm] | Formability & Handleability |
|---|---|---|---|---|---|
| Example 1 | 167 | 2 | 72 | 30 | 1 |
| Example 2 | 169 | 2 | 73 | 29 | 1 |
| Example 3 | 185 | 4 | 67 | 32 | 1 |
| Example 4 | 178 | 3 | 68 | 31 | 1 |
| Example 5 | 181 | 9 | 62 | 32 | 1 |
| Example 6 | 168 | 8 | 63 | 33 | 1 |
| Example 7 | 165 | 3 | 67 | 31 | 1 |
| Example 8 | 168 | 3 | 67 | 31 | 1 |
| Example 9 | 164 | 3 | 69 | 30 | 1 |
| Example 10 | 163 | 7 | 61 | 30 | 1 |
| Example 11 | 163 | 2 | 73 | 26 | 1 |
| Example 12 | 172 | 3 | 68 | 30 | 1 |
| Example 13 | 169 | 5 | 69 | 29 | 1 |
| Comparative Example 1 | 163 | 3 | 74 | 18 | 3 |
| Comparative Example 2 | 168 | 5 | 65 | 20 | 3 |
| Comparative Example 3 | 173 | 10 | 62 | 32 | 2 |
| Comparative Example 4 | 164 | 3 | 67 | 24 | 3 |
| Comparative Example 5 | 158 | 51 | 32 | 34 | 2 |
| Comparative Example 6 | 154 | 6 | 63 | 27 | 1 |
| Comparative Example 7 | 153 | 5 | 63 | 28 | 1 |
| Comparative Example 8 | 156 | 5 | 64 | 29 | 1 |

Table 4 shows that the flowable composite resins of Examples 1 through 13 have good flexural strength, abrasion resistance, extrusion strength, polishability, consistency, and formability and handleability.

In contrast, the flowable composite resins of Comparative Examples 1 through 3 and 6 contain the inorganic particles (A-4), (A-5) or (A-6) that are surface-treated with 3-methacryloyloxypropyltrimethoxysilane, and therefore cannot achieve both flexural strength and formability and handleability.

The formability and handleability of the flowable composite resin of Comparative Example 4 are degraded because the ratio of the mass of the inorganic particles (B-1) to the total mass of the inorganic particles (A-2) and the inorganic particles (B-1) is 0.06.

The flexural strength, the abrasion resistance, the polishability, and the formability and handleability of the flowable composite resin of Comparative Example 5 are degraded because of the inclusion of the inorganic particles (A-7) having a volume-median particle size of 2.0 μm.

The flexural strength of the flowable composite resins of Comparative Examples 7 and 8 is reduced because of the inclusion of the inorganic particles (B-2) that are surface-treated with 3-methacryloyloxypropyltrimethoxysilane.

The present international application is based upon and claims the benefit of priority of Japanese Patent Application No. 2015-058647, filed on Mar. 20, 2015, the entire contents of which are hereby incorporated herein by reference.

The invention claimed is:

1. A dental curable composition comprising:
a polymerizable monomer, inorganic particles (A), and inorganic particles (B),
wherein the inorganic particles (A) have a volume-median particle size of more than or equal to 0.1 μm and less than or equal to 0.9 μm and are surface-treated with a compound expressed by a general formula

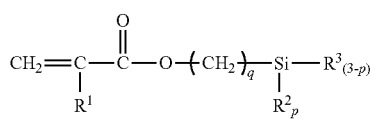

(where $R^1$ is a hydrogen atom or a methyl group, $R^2$ is a hydrolyzable group, $R^3$ is a hydrocarbon group having 1 to 6 carbon atoms, p is 2 or 3, and q is an integer greater than or equal to 8 and smaller than or equal to 13),
wherein the inorganic particles (B) have an average primary particle size of more than or equal to 5 nm and less than or equal to 50 nm, where at least one of a group expressed by a general formula

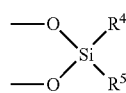

(where $R^4$ and $R^5$ are independently a methyl group or an ethyl group) and a group expressed by a general formula

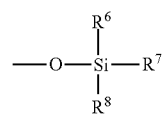

(where $R^6$, $R^7$, and $R^8$ are independently a methyl group or an ethyl group) is present at surfaces of the inorganic particles (B),
wherein a ratio of a mass of the inorganic particles (B) to a total mass of the inorganic particles (A) and the inorganic particles (B) is more than or equal to 0.02 and less than or equal to 0.05,
wherein a ratio of a mass of the polymerizable monomer to the total mass of the inorganic particles (A) and the inorganic particles (B) is 0.25 to 0.5, and
wherein an extrusion strength is less than or equal to 10 kgf.

2. The dental curable composition as claimed in claim 1, wherein the dental curable composition is a flowable composite resin.

3. A method of manufacturing a dental curable composition, the method comprising:
mixing a polymerizable monomer, inorganic particles (A), and inorganic particles (B),
wherein the inorganic particles (A) have a volume-median particle size of more than or equal to 0.1 μm and less than or equal to 0.9 μm and are surface-treated with a compound expressed by a general formula

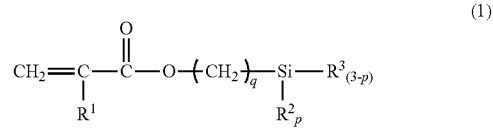

(where $R^1$ is a hydrogen atom or a methyl group, $R^2$ is a hydrolyzable group, $R^3$ is a hydrocarbon group having 1 to 6 carbon atoms, p is 2 or 3, and q is an integer greater than or equal to 8 and smaller than or equal to 13),
wherein the inorganic particles (B) have an average primary particle size of more than or equal to 5 nm and less than or equal to 50 nm, where at least one of a group expressed by a general formula

(where $R^4$ and $R^5$ are independently a methyl group or an ethyl group) and a group expressed by a general formula

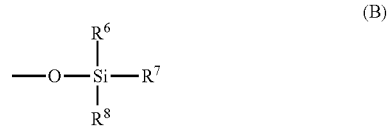

(where $R^6$, $R^7$, and $R^8$ are independently a methyl group or an ethyl group) is present at surfaces of the inorganic particles (B),
wherein a ratio of a mass of the inorganic particles (B) to a total mass of the inorganic particles (A) and the inorganic particles (B) is more than or equal to 0.02 and less than or equal to 0.05,
wherein a ratio of a mass of the polymerizable monomer to the total mass of the inorganic particles (A) and the inorganic particles (B) is 0.25 to 0.5, and
wherein an extrusion strength is less than or equal to 10 kgf.

4. The dental curable composition as claimed in claim 1, wherein the inorganic particles (A) are spherical.

* * * * *